(12) United States Patent
Kwon et al.

(10) Patent No.: US 7,812,154 B2
(45) Date of Patent: Oct. 12, 2010

(54) METHOD FOR PREPARING OXYTITANIUM PHTHALOCYANINE CHARGE GENERATING MATERIAL AND APPARATUS FOR PREPARING THE SAME

(75) Inventors: Jong Ho Kwon, Busan (KR); Ki Suck Jung, Busan (KR); Woo Ho Son, Busan (KR); Seong Soo Park, Busan (KR); Jin Phil Ko, Busan (KR); Hyun Suk Jung, Busan (KR)

(73) Assignee: Phthalos Co., Ltd, Busan (KR)

( * ) Notice: Subject to any disclaimer, the term of this patent is extended or adjusted under 35 U.S.C. 154(b) by 972 days.

(21) Appl. No.: 10/574,797

(22) PCT Filed: Oct. 7, 2004

(86) PCT No.: PCT/KR2004/002561

§ 371 (c)(1),
(2), (4) Date: Dec. 13, 2006

(87) PCT Pub. No.: WO2005/033803

PCT Pub. Date: Apr. 14, 2005

(65) Prior Publication Data

US 2007/0122725 A1 May 31, 2007

(30) Foreign Application Priority Data

Oct. 8, 2003 (KR) ................. 10-2003-0070060

(51) Int. Cl.
*C09B 47/08* (2006.01)
*C07D 47/00* (2006.01)
(52) U.S. Cl. ........................................ 540/145; 430/78
(58) Field of Classification Search ................. 540/145; 430/78
See application file for complete search history.

(56) References Cited

U.S. PATENT DOCUMENTS

| 4,664,997 A | 5/1987 | Suzuki et al. |
| 4,728,592 A | 3/1988 | Ohaku et al. |
| 4,898,799 A | 2/1990 | Fujimaki et al. |
| 4,971,877 A | 11/1990 | Miyamoto et al. |
| 4,994,339 A | 2/1991 | Kinoshita et al. |
| 5,039,586 A | 8/1991 | Itami et al. |
| 5,059,355 A | 10/1991 | Ono et al. |
| 5,132,197 A | 7/1992 | Iuchi et al. |
| 5,164,493 A | 11/1992 | Mayo et al. |
| 5,194,354 A | 3/1993 | Takai et al. |
| 5,213,929 A | 5/1993 | Takano et al. |
| 5,252,417 A | 10/1993 | Tokida et al. |
| 5,298,353 A | 3/1994 | Ohmori |
| 5,350,844 A | 9/1994 | Martin et al. |
| 5,567,559 A | 10/1996 | Yang et al. |
| 5,593,805 A | 1/1997 | Go et al. |
| 5,773,184 A | 6/1998 | Fuller, Jr. et al. |
| 5,786,121 A | 7/1998 | Richter et al. |
| 5,972,551 A | 10/1999 | Miyauchi et al. |
| 6,225,015 B1 | 5/2001 | Okaji et al. |
| 6,284,420 B1 | 9/2001 | Liu et al. |
| 6,447,965 B1 | 9/2002 | Nakamura et al. |
| 6,485,658 B1 | 11/2002 | Horiuchi et al. |
| 6,521,387 B2 | 2/2003 | Kawasaki |

FOREIGN PATENT DOCUMENTS

| JP | 62-256865 | 11/1987 |
| KR | 1994-7962 | 8/1994 |

(Continued)

OTHER PUBLICATIONS

Yao, Jiachang et al., "A Convenient Synthetic Method for Pure Oxo (phthalocyaninato) titanium (IV) and Application to Other Metal Phthalocyanines" Bull. Chem. Soc. Jpn., vol. 68, No. 3, pp. 1001-1005, 1995.

(Continued)

*Primary Examiner*—James O. Wilson
*Assistant Examiner*—Paul V. Ward
(74) *Attorney, Agent, or Firm*—Oblon, Spivak, McClelland, Maier & Neustadt, L.L.P.

(57) ABSTRACT

Disclosed herein are a method and an apparatus for preparing oxytitanium phthalocyanine as a charge generating material. The method comprises the steps of homogeneously mixing an oxytitanium phthalocyanine crude with an organic solvent while microwave energy having a frequency of 0.1~100 GHz and a power of 10~3,000 W and ultrasonic wave energy having a frequency of 1~1,000 kHz and a power of 10~5,000 W are applied thereto, and reacting the mixture at 30~100° C. for 0.5~5 hours. The apparatus comprises: a magnetron 1 capable of generating a frequency of 0.1~100 GHz and a power of 100~3,000 W; a mode stirrer 3 for making the wavelength of microwaves uniform in a microwave container 2; a PID type temperature controller 9 for accurately measurement and controlling the temperature of reactants; a K-type thermocouple shielded from microwaves 4; a condenser 5; an agitator 6, the thermocouple 4, the condenser 5 and the agitator 6 being inserted into three openings formed at a top of the microwave container 2; an ultrasonic tip 7 inserted into an opening formed at a bottom of the microwave container 2; a Pyrex container 9 into which the reactants are introduced; and a solvent tank 10. According to the method and the apparatus, an oxytitanium phthalocyanine charge generating material having superior thermal stability and crystal stability can be prepared in an efficient manner.

20 Claims, 8 Drawing Sheets

FOREIGN PATENT DOCUMENTS

| | | |
|---|---|---|
| KR | 2003-0022179 | 3/2003 |
| KR | 2003-0022831 | 3/2003 |
| KR | 2003-0058987 | 7/2003 |
| KR | 2003-0058988 | 7/2003 |
| KR | 2003-0086508 | 11/2003 |
| KR | 2003-0086509 | 11/2003 |

OTHER PUBLICATIONS

U.S. Appl. No. 10/556,785, filed Nov. 14, 2005, Kwon, et al.

METHOD FOR PREPARING OXYTITANIUM PHTHALOCYANINE CHARGE GENERATING MATERIAL AND APPARATUS FOR PREPARING THE SAME

This application is a 371 of PCT/KR04/02561 filed Oct. 7, 2004.

TECHNICAL FIELD

The present invention relates to a method and an apparatus for preparing oxytitanium phthalocyanine suitable as a charge generating material. More particularly, the present invention relates to a method for preparing oxytitanium phthalocyanine as a charge generating material having superior crystal stability by using both ultrasonic waves and microwaves, and an apparatus for implementing the method.

BACKGROUND ART

Photoconductors are highly photosensitive in the visible region, and are widely used in various devices, such as copying machines, printers, etc. Most of the currently used photoconductors are produced by applying a photosensitive layer including an inorganic charge generating material selected from selenium, zinc oxide, cadmium sulfide and others as a main component to a conductive substrate. However, these inorganic charge generating materials are still unsatisfactory in photosensitivity, thermal stability, water resistance, durability and other physical properties required in copying machines and printers. For example, photoconductors using cadmium sulfide suffer from poor water resistance and durability, and photoconductors using zinc oxide have a problem in terms of low durability. Further, photoconductors using selenium and cadmium sulfide are limited in their production and handling.

In an effort to solve the problems of the inorganic charge generating materials, a great deal of research has been conducted on organic charge generating materials. Of these, oxytitanium phthalocyanine is widely used due to its superior photosensitivity, durability, thermal stability, etc.

Oxytitanium phthalocyanine is known to exist in various crystal forms. Representative crystal forms are alpha-form (B- or II-form), beta-form (A- or I-form), meta-form (C- or III-form), gamma-form (D- or IV-form), and the like. Of these, since the gamma-form oxytitanium phthalocyanine has better electrophotographic characteristics than the other forms, it is widely used as a charge generating material. Since oxytitanium phthalocyanine exhibits different electrophotographic characteristics depending on its X-ray diffraction patterns, oxytitanium phthalocyanine characterized by its X-ray diffraction patterns is protected by patents assigned to a number of manufacturing companies. U.S. Pat. No. 5,132,197 discloses oxytitanium phthalocyanine showing X-ray diffraction characteristic peaks at Bragg angles of 9.0°, 14.2°, 23.9°, and 27.1°. U.S. Pat. No. 5,194,354 discloses oxytitanium phthalocyanine showing X-ray diffraction peaks at Bragg angles of: 7.2°, 14.2°, 24.0° and 27.2°; 7.4°, 10.9° and 17.9°; 7.6°, 9.7°, 12.7°, 16.2° and 26.4°; or 8.5° and 10.2°. U.S. Pat. No. 5,298,353 discloses oxytitanium phthalocyanine showing X-ray diffraction peaks at Bragg angles of: 9.0°, 14.2°, 23.9° and 27.1°; or 7.4°, 9.2°, 10.4°, 11.6°, 13.0°, 14.3°, 15.0°, 15.5°, 23.4°, 24.1°, 26.2° and 27.2°. U.S. Pat. No. 5,593,805 discloses oxytitanium phthalocyanine showing X-ray diffraction peaks at Bragg angles of 7.4°, 10.2°, 12.5°, 15.0°, 16.3°, 18.3°, 22.4°, 24.2°, 25.2°, and 28.5°. U.S. Pat. No. 4,728,592 discloses oxytitanium phthalocyanine showing X-ray diffraction peaks at Bragg angles of 7.6°, 10.2°, 12.6°, 13.2°, 15.1°, 16.2°, 17.2°, 18.3°, 22.5°, 24.2°, 25.3°, 28.6°, 29.3°, and 31.5°. U.S. Pat. No. 5,252,417 discloses oxytitanium phthalocyanine showing X-ray diffraction peaks at Bragg angles of 9.5°, 14.3°, 18.0°, 24.0°, and 27.2°. U.S. Pat. No. 5,567,559 discloses oxytitanium phthalocyanine showing X-ray diffraction peaks at Bragg angles of: 7.5°, 9.3°, 13.6°, 14.3°, 17.9°, 24.0°, 27.2° and 29.1°; or 7.4°, 9.5°, 11.6°, 13.6°, 14.3°, 17.9°, 24.0°, 27.2° and 29.1°. U.S. Pat. No. 6,284,420 discloses oxytitanium phthalocyanine showing X-ray diffraction peaks at Bragg angles of 7.3°, 9.4°, 14.0°, 24.1°, 25.7°, 27.2°, and 28.5°. U.S. Pat. No. 4,898,799 discloses oxytitanium phthalocyanine showing X-ray diffraction peaks at Bragg angles of 9.5°, 11.7°, 15.0°, 23.5°, 24.1°, and 27.3°. U.S. Pat. No. 4,994,339 discloses oxytitanium phthalocyanine showing X-ray diffraction peaks at Bragg angles of 9.6°, 11.7°, 24.1°, and 25.2°. U.S. Pat. No. 5,039,586 discloses oxytitanium phthalocyanine showing X-ray diffraction peaks at Bragg angles of 6.8°, 9.5°, 11.5°, 13.4°, 18.0°, 24.1°, and 27.3°. U.S. Pat. No. 4,664,997 discloses oxytitanium phthalocyanine showing X-ray diffraction peaks at Bragg angles of 9.3°, 10.6°, 13.2°, 15.1°, 15.7°, 16.1°, 20.8°, 23.3°, 26.3°, and 27.1°. U.S. Pat. No. 5,213,929 discloses oxytitanium phthalocyanine showing X-ray diffraction peaks at Bragg angles of 7.4°, 22.3°, 24.1°, 25.3°, 27.3°, and 28.5°. U.S. Pat. No. 5,972,551 discloses oxytitanium phthalocyanine showing X-ray diffraction peaks at Bragg angles of 7.4°, 9.4°, 9.7°, and 27.3°. U.S. Pat. No. 6,447,965 discloses oxytitanium phthalocyanine showing X-ray diffraction peaks at Bragg angles of 7.3°, 9.4°, 9.6°, 11.6°, 13.3°, 17.9°, 24.1°, and 27.2°. U.S. Pat. No. 5,350,844 discloses oxytitanium phthalocyanine showing X-ray diffraction peaks at Bragg angles of 6.8°, 9.2° 10.4°, 12.3°, 13.1°, 15.0°, 15.6°, 16.0°, 20.6°, 23.2°, 25.3°, 26.2°, 26.5°, and 27.1°. The oxytitanium phthalocyanine charge generating material prepared by the method of the present invention is characterized in that it shows X-ray diffraction characteristic peaks at Bragg angles of 7.2°, 9.6°, 11.7°, 12.7°, 13.4°, 14.1°, 14.8°, 18.0°, 18.4°, 22.3°, 24.1°, and 27.2°, the strongest peak at a Bragg angle of 27.2°, the second strongest peak at a Bragg angle of 9.6°, single peaks having no splitting at Bragg angles of 9.6° and 24.1°, and no diffraction peak at a Bragg angle of 26°~28°. The Bragg angle used herein is a 2theta value and has an error range of ±0.2°.

Oxytitanium phthalocyanine is commonly synthesized by reacting 1,2-dicyanobenzene or 1,3-diiminoisoindoline as a main material with titanium tetrachloride or tetraalkoxy titanium as a titanium source in N-methylpyrrolidone, 1-chloronaphthalene or quinoline as a solvent at 160~200° C. for 6~12 hours, and purifying the obtained reaction product. The final product is strictly defined as "oxytitanium phthalocyanine in a crude state (hereinafter, referred to as an "oxytitanium phthalocyanine crude")". Japanese Patent No. 62-256865 describes a method for preparing oxytitanium phthalocyanine by using 1,2-dicyanobenzene and titanium tetrachloride, U.S. Pat. No. 4,971,877 describes a method for preparing oxytitanium phthalocyanine by using 1,3-diiminoisoindoline and tetraalkoxy titanium, and *Bull. Chem. Soc. Jpn.*, 68, 1001-1005, 1995 reports a method for preparing oxytitanium phthalocyanine by using 1,2-dicyanobenzene and tetrabutoxytitanium. Since the oxytitanium phthalocyanine crudes cannot be directly used as charge generating materials due to their large particle size and poor electrophotographic characteristics, they must undergo an appropriate post treatment process in order to be used as highly photosensitive charge generating materials. The structural formula of oxytitanium phthalocyanine is represented by the following Formula 1:

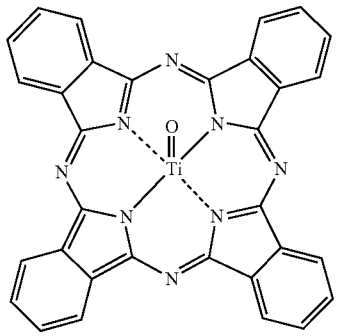

Formula 1

A representative post-treatment process of an oxytitanium phthalocyanine crude is one wherein the oxytitanium phthalocyanine crude is dissolved in concentrated sulfuric acid or hyperchlorinated carboxylic acid, recrystallized from various organic solvents, such as water, and treated with a halogenated aromatic solvent, such as a halobenzene or halonaphthalene, to prepare an oxytitanium phthalocyanine charge generating material. U.S. Pat. No. 5,164,493 describes a method for preparing oxytitanium phthalocyanine by using concentrated sulfuric acid and chlorobenzene. U.S. Pat. No. 5,252,417 describes a method for preparing oxytitanium phthalocyanine by using trifluoroacetic acid and chlorobenzene. U.S. Pat. No. 5,786,121 describes a method for preparing oxytitanium phthalocyanine by using pentafluoropropionic acid and chlorobenzene. U.S. Pat. No. 6,521,387 describes a method for preparing oxytitanium phthalocyanine by using concentrated sulfuric acid and 1,2-dichloroethane. U.S. Pat. No. 5,773,184 describes a method for preparing oxytitanium phthalocyanine by using difluoroacetic acid or dichloroacetic acid.

Another representative post-treatment process of an oxytitanium phthalocyanine crude is one wherein the oxytitanium phthalocyanine crude is dry-ground using a grinder, such as a ball mill, vibration mill or attritor, and is then treated with organic solvents. U.S. Pat. No. 5,567,559 describes a method for preparing oxytitanium phthalocyanine by using a ball mill and n-butyl ether, and U.S. Pat. No. 5,059,355 describes a method for preparing oxytitanium phthalocyanine by using a paint shaker and 1,2-dichlorobenzene.

The oxytitanium phthalocyanine charge generating materials are advantageous in terms of their superior electrophotographic characteristics, but have a disadvantage of poor crystal instability in organic solvents, e.g., tetrahydrofuran. Due to this disadvantage, when the oxytitanium phthalocyanine is used to prepare a coating solution for a charge generating layer, the storage stability is extremely deteriorated, leading to a shortened shelf life. In addition, when the oxytitanium phthalocyanine is dissolved in an acid or ground, followed by the treatment with an organic solvent, it is highly sensitive to temperature and thus a considerable care must be taken to control the temperature in the treatment with the organic solvent. It appears that because the crystal form of the oxytitanium phthalocyanine is not completely transformed into gamma-form and a small quantity of beta- or alpha-form crystal remains, the previously formed gamma-form crystal is easily transformed into the more stable beta- or alpha-form crystal.

DISCLOSURE OF THE INVENTION

Therefore, the present invention has been made in view of the above problems, such as complex processes arising from poor crystal stability and temperature sensitivity, and it is an object of the present invention to provide a method for preparing oxytitanium phthalocyanine as a high-quality charge generating material by preparing a novel crystal-form oxytitanium phthalocyanine crude showing one X-ray diffraction peak at a Bragg angle of 27.2±0.20 by means of both microwaves and ultrasonic waves, and subjecting the oxytitanium phthalocyanine crude to post-treatment.

It is another object of the present invention to provide an apparatus for preparing oxytitanium phthalocyanine as a charge generating material: comprising a magnetron 1 capable of generating a frequency of 0.1~100 GHz and a power of 100~3,000 W; a mode stirrer 3 for making the wavelength of microwaves uniform in a microwave container 2; a PID type temperature controller 8 for accurately measuring and controlling the temperature of reactants; a K-type thermocouple 4 shielded from microwaves; a condenser 5; an agitator 6, the thermocouple 4, the condenser 5 and the agitator 6 being inserted into three openings formed at the top of the microwave container 2; an ultrasonic tip 7 inserted into an opening formed at the bottom of the microwave container 2; a Pyrex container 9 into which the ractants are introduced; and a solvent tank 10.

It is another object of the present invention to provide a high-quality oxytitanium phthalocyanine charge generating material prepared by the method.

It is still another object of the present invention to provide a photoconductor produced using the oxytitanium phthalocyanine charge generating material.

In accordance with one aspect of the present invention, there is provided a method for preparing oxytitanium phthalocyanine as a charge generating material, comprising the steps of: homogeneously mixing an oxytitanium phthalocyanine crude with an organic solvent while microwave energy having a frequency of 0.1~100 GHz and a power of 10~3,000 W and ultrasonic wave energy having a frequency of 1~1,000 kHz and a power of 10~5,000 W are applied thereto; and reacting the mixture at 30~100° C. for 0.5~5 hours.

In accordance with another aspect of the present invention, there is provided an apparatus for preparing oxytitanium phthalocyanine as a charge generating material, comprising: a magnetron 1 capable of generating a frequency of 0.1~100 GHz and a power of 100~3,000 W; a mode stirrer 3 for making the wavelength of microwaves uniform in a microwave container 2; a PID type temperature controller 8 for accurately measuring and controlling the temperature of reactants; a K-type thermocouple 4 shielded from microwaves; a condenser 5; an agitator 6, the thermocouple 4, the condenser 5 and the agitator 6 being inserted into three openings formed at the top of the microwave container 2; an ultrasonic tip 7 inserted into an opening formed at the bottom of the microwave container 2; a Pyrex container 9 into which the reactants are introduced; and a solvent tank 10, wherein an oxytitanium phthalocyanine crude is homogeneously mixed with an organic solvent within the Pyrex container 9 while microwave energy having a frequency of 0.1~100 GHz and a power of 10~3,000 W and ultrasonic wave energy having a frequency of 1~1,000 kHz and a power of 10~5,000 W are applied thereto, and the reactants are reacted with each other at a temperature of 30~100° C. for 0.5~5 hours while the temperature of the reactants is accurately controlled by the K-type thermocouple 4 and the PID type temperature controller 8.

In accordance with another aspect of the present invention, there is provided an oxytitanium phthalocyanine charge generating material prepared by the method.

In accordance with still another aspect of the present invention, there is provided a photoconductor produced using the oxytitanium phthalocyanine charge generating material.

BRIEF DESCRIPTION THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
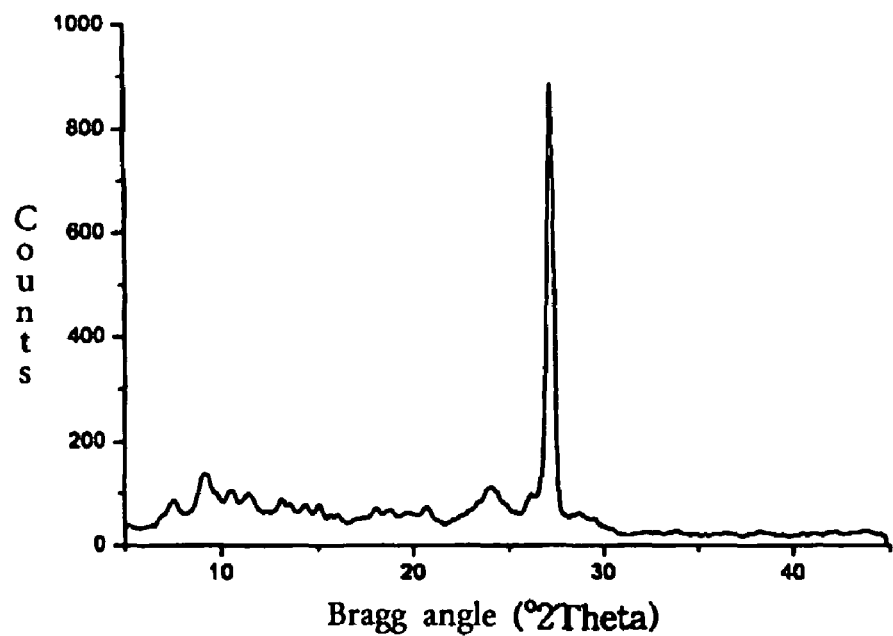
FIG. 1 is a graph showing the X-ray diffraction pattern of an oxytitanium phthalocyanine crude prepared in Example 1 (Synthesis 1) of the present invention.

Hereinafter, the present invention will be explained in more detail.

The present invention provides a method for preparing oxytitanium phthalocyanine as a charge generating material by using both microwaves and ultrasonic waves.

Specifically, an oxytitanium phthalocyanine crude is homogeneously mixed with an organic solvent while microwaves are applied thereto, and then the mixture is reacted by heating.

The oxytitanium phthalocyanine crude used herein may be obtained by various processes commonly known in the art. U.S. Pat. No. 4,971,877 describes a method for preparing an oxytitanium phthalocyanine crude by using 1,3-diiminoisoindoline and tetraalkoxy titanium, and *Bull. Chem. Soc. Jpn.*, 68, 1001-1005, 1995 reports a method for preparing an oxytitanium phthalocyanine crude by using 1,2-dicyanobenzene and tetrabutoxy titanium. The former method uses a general synthesis apparatus, whereas the latter method uses a synthesis apparatus using both microwaves and ultrasonic waves (see, Korean Patent Application No. 10-2003-0030726). Specifically, the oxytitanium titanium crude can be synthesized by reacting 1,2-dicyanobenzene or 1,3-diiminoisoindoline as a main material with titanium tetrachloride or tetraalkoxy titanium as a titanium source in N-methylpyrrolidone, 1-chloronaphthalene or quinoline as a solvent at 160~200° C. for 0.1~12 hours, and purifying the obtained reaction product. At this time, the reaction can be carried out using a conventional or microwave synthesis apparatus.

The oxytitanium phthalocyanine crude is preferably dissolved in an acid at room temperature or more and recrystallized, or dry- or wet-ground before use. At this time, the acid is preferably sulfuric acid, phosphoric acid or a halogenated carboxylic acid. Examples of preferred solvents used for the recrystallization include water, aliphatic and aromatic alcohols, ketones, ethers, esters and mixed solutions thereof. As preferred aliphatic alcohols, there may be mentioned methanol, ethanol, propanol, isopropanol, butanol, and isobutanol. Examples of preferred aromatic alcohols include benzyl alcohol and the like. Examples of preferred ketones include acetone, methyl ethyl ketone, N-methylpyrrolidone, and tetrahydrofuran. Examples of preferred ethers include, ethyl ether, and n-butyl ether. Examples of preferred esters include methyl acetate and ethyl acetate.

As preferred organic solvents, there can be used halogenated benzenes, halogenated naphthalenes, and aqueous solutions thereof. An aqueous solution of the halogenated benzene and the halogenated naphthalene is more preferred. At this time, the mixing ratio of water to the halogenated benzene or naphthalene is in the range between 1:1 and 10:1. The term "halogenated benzene or naphthalene" refers to benzene or naphthalene substituted with at least one halogen atom, such as chlorine, fluorine, bromine, or iodine. The number of the substituents is preferably 1 to 4.

The mixing ratio between the organic solvent and the oxytitanium phthalocyanine crude is not particularly limited, but is preferably in the range between 1:1 and 10:1.

The microwaves are preferably applied at a frequency of 0.1~100 GHz and a power of 10~3,000 W. When the microwaves are out of these ranges, accurate temperature control is difficult, and uniform heating and volume heating, which are characteristics of microwaves, cannot be appropriately utilized. The reaction temperature is within the range of 30 to 100° C. When the reaction temperature is out of this range, the crystal form of the oxytitanium phthalocyanine is not completely transformed into gamma-form and a quantity of beta- or alpha-form crystal remains, which causes the problem that the previously formed gamma-form crystal in the organic solvent at a high temperature is easily transformed into the more stable beta- or alpha-form crystal. Accordingly, the reaction is preferably carried out at a temperature of 50~70° C. for 0.5~5 hours. When the reaction time is less than 0.5 hours, the crystal transformation into the gamma-form is insufficient. Meanwhile, when the reaction time exceeds 5 hours, the previously formed gamma-form crystal may be again transformed into the more stable beta- or alpha-form crystal. Preferably, the reaction time is in the range of from 10 minutes to 5 hours.

According to the method of the present invention, an oxytitanium phthalocyanine charge generating material is prepared by the following procedure.

First, the oxytitanium phthalocyanine crude is dissolved in concentrated sulfuric acid and stirred for 2 hours. Thereafter, the sulfuric acid solution is recrystallized from ice-water. The recrystallized oxytitanium phthalocyanine crude is separated by filtration, and washed with water until the filtrate is neutralized. The obtained oxytitanium phthalocyanine cake is dispersed in a mixed solution of water and chlorobenzene, and is then treated in a microwave-generating apparatus at 60° C. for one hour.

Figure 3:
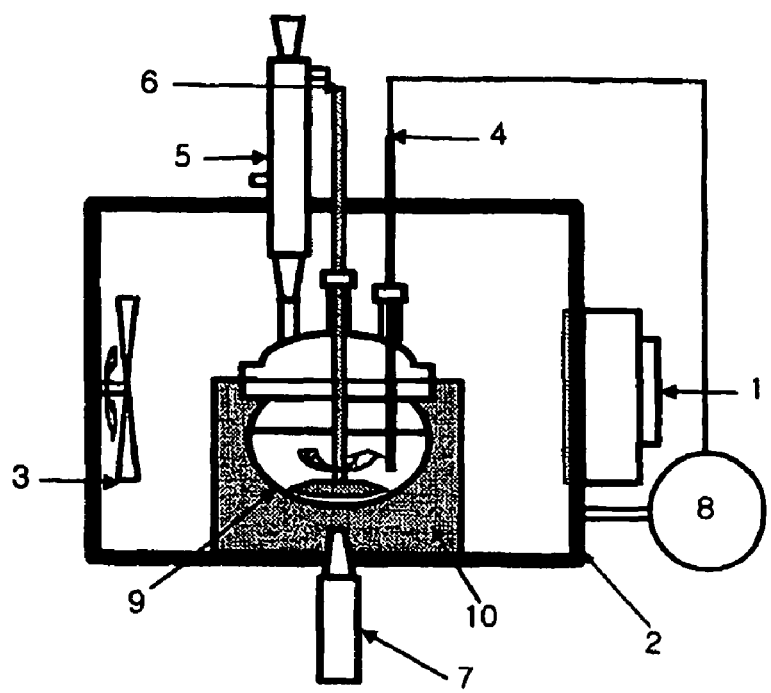
FIG. 3 is a view schematically showing the structure of a microwave-generating apparatus used in the present invention.

The microwave-generating apparatus used in the present invention is shown in FIG. 3. The microwave-generating apparatus comprises: a magnetron 1 capable of generating a frequency of 2.45 GHz and a power of 3,000 W; a mode stirrer 3 for making the wavelength of microwaves uniform in a microwave container 2; a K-type thermocouple 4 shielded from microwaves and a PID type temperature controller 8 made of stainless steel for accurately measuring and controlling the temperature of reactants; a separation-type three-neck Pyrex container 9 disposed in the center of the microwave container 2 and insulated with glass fiber for better heat efficiency of the reactants; a condenser 5; an agitator 6, the thermocouple 4, the condenser 5 and the agitator 6 being inserted into three openings (diameter: about 1 cm) formed at the top of the microwave container 2; an ultrasonic tip 7 inserted into an opening (diameter: about 1 cm) formed at the bottom of the microwave container 2; and a solvent tank 10 filled with decahydronaphthalene (decalin) capable of transferring ultrasonic wave energy to the reactants without any reaction with microwaves.

Using the synthesis apparatus of the present invention, the oxytitanium phthalocyanine crude is homogeneously mixed with the organic solvent in the Pyrex container 9 while microwaves having a frequency of 0.1~100 GHz and a power of 10~3,000 W and ultrasonic waves having a frequency of 1~1,000 GHz and a power of 10~5,000 W are applied thereto, and then the resulting mixture is reacted at 30~100° C. for 0.5~5 hours while the temperature is accurately controlled using the K-type thermocouple 4 shielded from microwaves and the PID type temperature controller 8, to prepare an oxytitanium phthalocyanine charge generating material. After the treatment with microwaves, the mixture is filtered, washed with methanol, and dried in a drier.

As can be seen from the X-ray diffraction patterns of the oxytitanium phthalocyanine charge generating materials prepared using both microwaves and ultrasonic waves, no diffraction peak is observed at a Bragg angle of 26.1±0.2° (see FIGS. 4~6 and 12). This observation indicates that the crystal is completely transformed into gamma-form. The scanning electron micrographs show that the particle size is considerably small and uniform when microwaves and ultrasonic waves are used. Accordingly, when the oxytitanium phthalocyanine charge generating materials are used to prepare a coating solution for a charge generating layer, the dispersion time can be shortened and thus the productivity of the oxytitanium phthalocyanine charge generating materials is enhanced (see FIGS. 14 and 15).

The oxytitanium phthalocyanine charge generating materials prepared by the method of the present invention have X-ray diffraction characteristic peaks at Bragg angles of 7.2±0.2°, 9.6±0.2°, 11.7±0.2°, 12.7±0.2°, 13.4±0.2°, 14.1±0.2°, 14.8±0.2°, 18.0±0.2°, 18.4±0.2°, 22.3±0.2°, 23.4±0.2°, 24.1±0.2°, 24.5±0.2°, and 27.2±0.2°.

The oxytitanium phthalocyanine charge generating materials can be effectively used in the production of photoconductors, particularly organic photoconductors.

The present invention will now be described in more detail with reference to the following examples and comparative examples. However, these examples are not to be construed as limiting the scope of the invention.

Example 1

Synthesis of Oxytitanium Phthalocyanine Crude

Synthesis 1

51.26 g of 1,2-dicyanobenzene, 12.14 g of urea, 34.38 g of tetrabutoxybenzene, and 100 g of nonanol were charged into a Pyrex container 9 in the synthesis apparatus of the present invention shown in FIG. 3. Thereafter, the reactants were homogeneously stirred at 160~170° C. for 0.1~6 hours while microwaves and ultrasonic wave energy at 28 kHz and 250 W was applied thereto, to prepare an oxytitanium phthalocyanine crude. During the reaction, the temperature of the reactants was accurately controlled using a PID type temperature controller 8 within an error range of ±1° C. At this time, the microwave power was controlled to the range of 10~3,000 W. The microwaves and the ultrasonic wave energy were simultaneously used from the initial stage of the reaction. The X-ray diffraction pattern of the oxytitanium phthalocyanine crude is shown in FIG. 1.

Synthesis 2

12.5 g of 1,3-diiminoisoindoline, 29.31 g of tetrabutoxybenzene, and 100 g of quinoline were charged into a Pyrex container in a conventional synthesis apparatus, and then the reactants were homogeneously stirred at 170~180° C. for 0.1~6 hours to prepare an oxytitanium phthalocyanine crude. The X-ray diffraction pattern of the oxytitanium phthalocyanine crude is shown in FIG. 1.

Example 2

300 g of 97% sulfuric acid was placed in a beaker, and stirred. While the temperature of the sulfuric acid was maintained at 10° C. or less, 10 g of the oxytitanium phthalocyanine crude prepared in Synthesis 2 of Example 1 was slowly dissolved and stirred for 2 hours. After the sulfuric acid solution was slowly poured on ice-water to recrystallize the oxytitanium phthalocyanine crude, the oxytitanium phthalocyanine crude was separated by filtration and washed with water until the pH of the filtrate was 7.0. The resulting oxytitanium phthalocyanine cake was added to a mixed solution of chlorobenzene (100 ml) and water (100 ml, including water contained in the cake), and was put into a microwave-generating apparatus. The reactants were heated to 50° C. using the PID type temperature controller for 30 minutes, stirred at 50° C. for one hour, and allowed to cool to room temperature. The cooled reactants were filtered to separate oxytitanium phthalocyanine, and washed with methanol. The oxytitanium phthalocyanine was dried in a drier to yield 9.8 g of an oxytitanium phthalocyanine charge generating material. The X-ray diffraction pattern of the oxytitanium phthalocyanine charge generating material was obtained under the following conditions:

X-ray bulb: Cu
Cu K-alpha wavelength (Å): 1.54056
Voltage (kV): 40.0
Current (mA): 100.0
Starting angle (°2 Theta): 5.00
Stopping angle (°2 Theta): 45.00
Stepping angle (°2 Theta): 0.020

Figure 4:
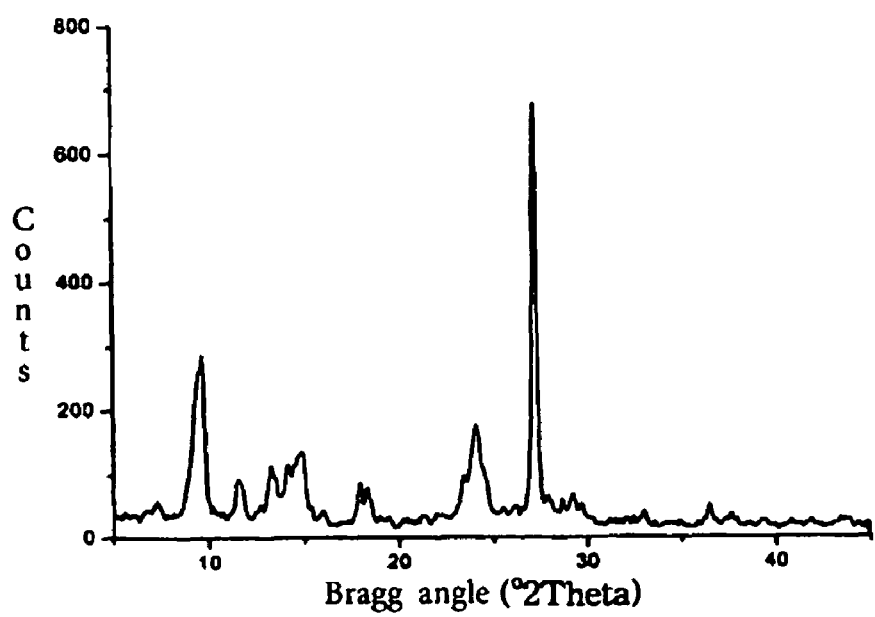
FIG. 4 is a graph showing the X-ray diffraction pattern of oxytitanium phthalocyanine prepared in Example 2 of the present invention.

The X-ray diffraction pattern of the oxytitanium phthalocyanine charge generating material is shown in FIG. 4.

Figure 14:
FIG. 14 is a scanning electron micrograph (SEM, 30,000×) of oxytitanium phthalocyanine prepared in Example 2 of the present invention.

The scanning electron micrograph (30,000×) of the oxytitanium phthalocyanine charge generating material is shown in FIG. 14.

Example 3

Figure 5:
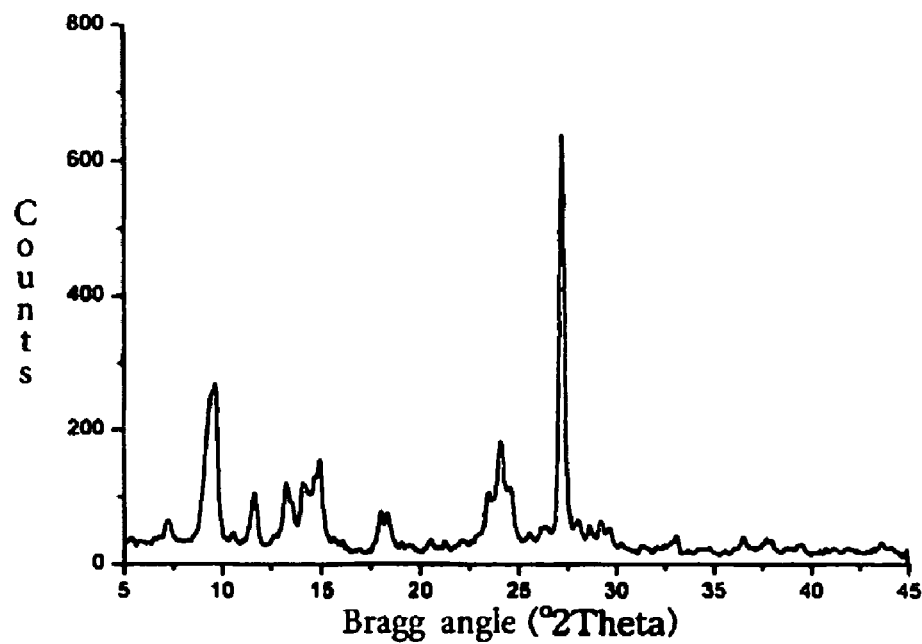
FIG. 5 is a graph showing the X-ray diffraction pattern of oxytitanium phthalocyanine prepared in Example 3 of the present invention.

9.8 g of an oxytitanium phthalocyanine charge generating material was prepared in the same manner as in Example 2, except that the microwave treatment was carried out at 60° C. The X-ray diffraction pattern of the oxytitanium phthalocyanine charge generating material is shown in FIG. 5.

Example 4

Figure 6:
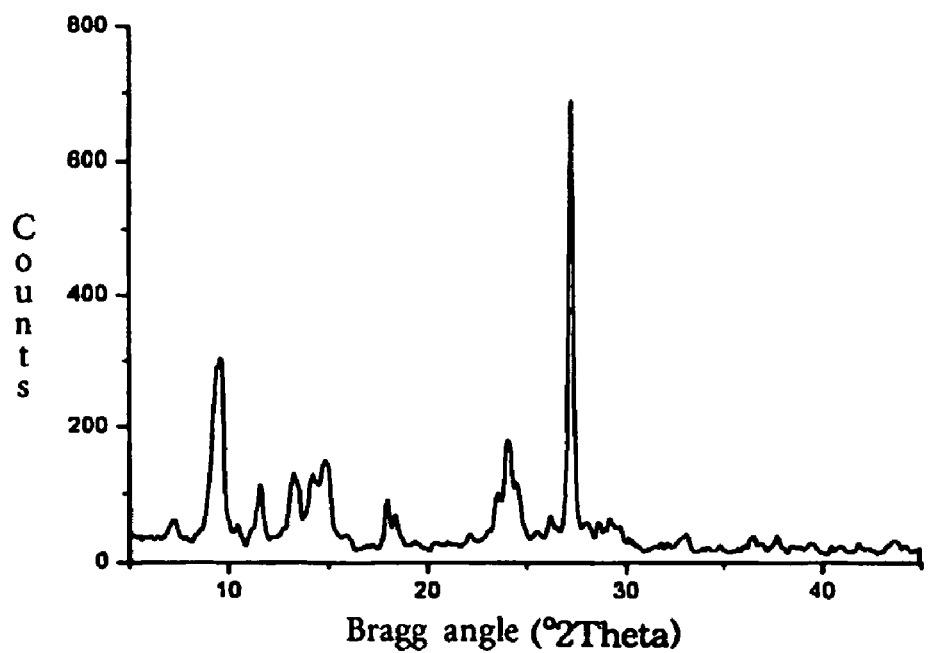
FIG. 6 is a graph showing the X-ray diffraction pattern of oxytitanium phthalocyanine prepared in Example 4 of the present invention.

9.8 g of an oxytitanium phthalocyanine charge generating material was prepared in the same manner as in Example 2, except that the microwave treatment was carried out at 70° C. The X-ray diffraction pattern of the oxytitanium phthalocyanine charge generating material is shown in FIG. 6.

Comparative Example 1

Figure 7:
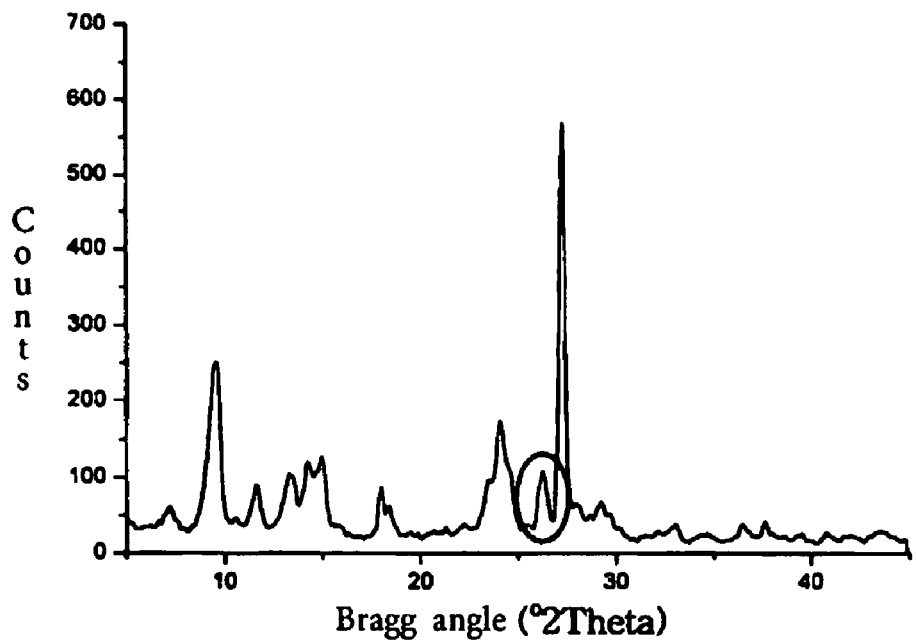
FIG. 7 is a graph showing the X-ray diffraction pattern of oxytitanium phthalocyanine prepared in Comparative Example 1 of the present invention (the circle shows a characteristic peak of beta-form oxytitanium phthalocyanine)
Figure 15:
FIG. 15 is a scanning electron micrograph (SEM, 30,000×) of oxytitanium phthalocyanine prepared in Comparative Example 2 of the present invention.
Figure 16:
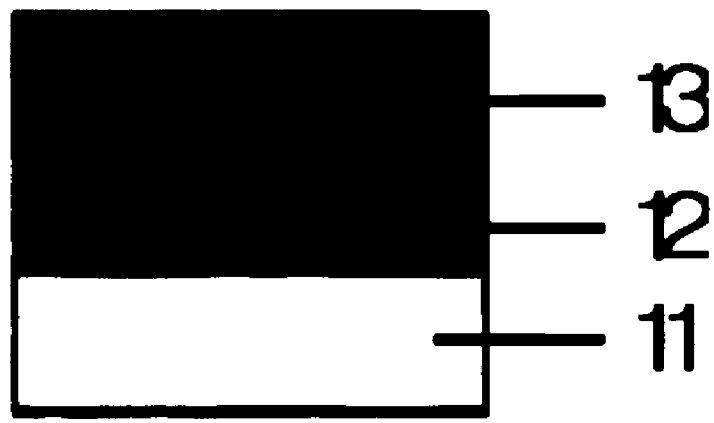
FIG. 16 is a cross-sectional view of a photoconductor drum used for the measurement of the electrical properties of oxytitanium phthalocyanine in the present invention.

9.8 g of an oxytitanium phthalocyanine charge generating material was prepared in the same manner as in Example 2, except that a magnetic heating stirrer was used as a conventional heat source instead of the microwave treatment. The X-ray diffraction pattern of the oxytitanium phthalocyanine charge generating material is shown in FIG. 7. The scanning electron micrograph (30,000×) of the oxytitanium phthalocyanine charge generating material is shown in FIG. 15.

Comparative Example 2

Figure 8:
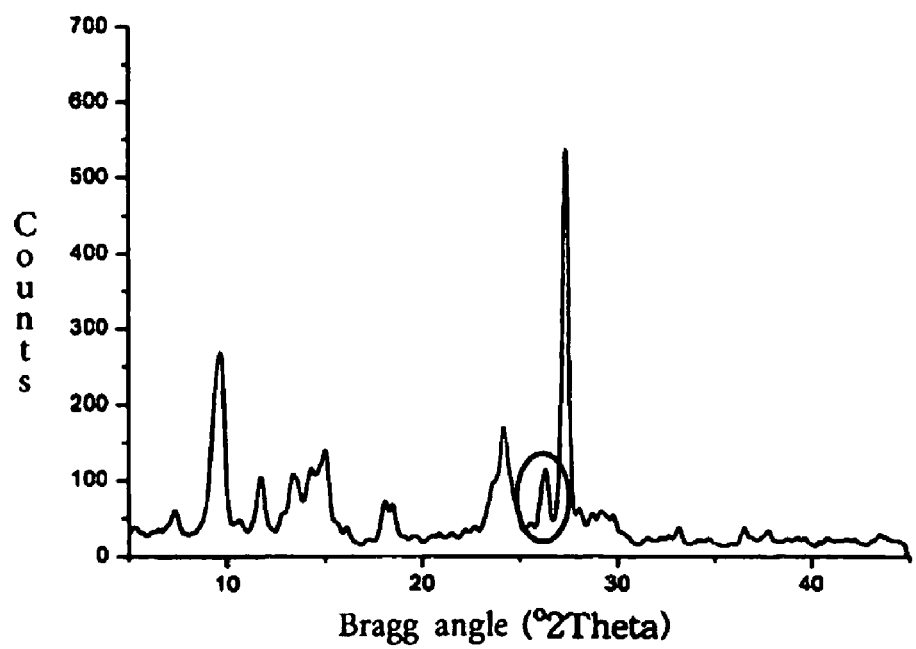
FIG. 8 is a graph showing the X-ray diffraction pattern of oxytitanium phthalocyanine prepared in Comparative Example 2 of the present invention (the circle shows a characteristic peak of beta-form oxytitanium phthalocyanine)

9.8 g of an oxytitanium phthalocyanine charge generating material was prepared in the same manner as in Example 3, except that a magnetic heating stirrer was used as a conventional heat source instead of the microwave treatment. The X-ray diffraction pattern of the oxytitanium phthalocyanine charge generating material is shown in FIG. 8.

Comparative Example 3

Figure 9:
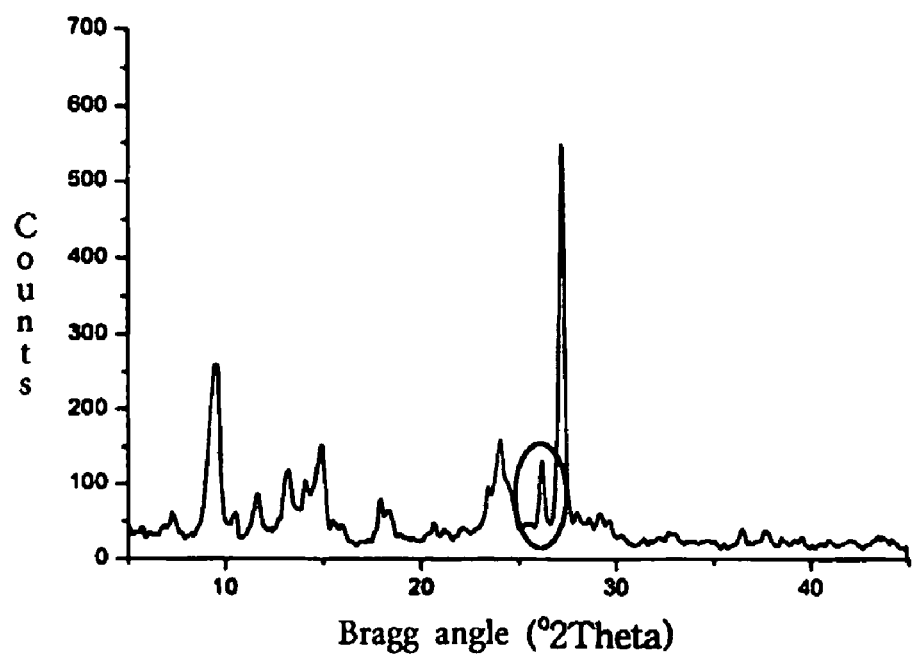
FIG. 9 is a graph showing the X-ray diffraction pattern of oxytitanium phthalocyanine prepared in Comparative Example 3 of the present invention (the circle shows a characteristic peak of beta-form oxytitanium phthalocyanine)

9.8 g of an oxytitanium phthalocyanine charge generating material was prepared in the same manner as in Example 4, except that a magnetic heating stirrer was used as a conventional heat source instead of the microwave treatment. The X-ray diffraction pattern of the oxytitanium phthalocyanine charge generating material is shown in FIG. 9.

Example 5

Figure 10:
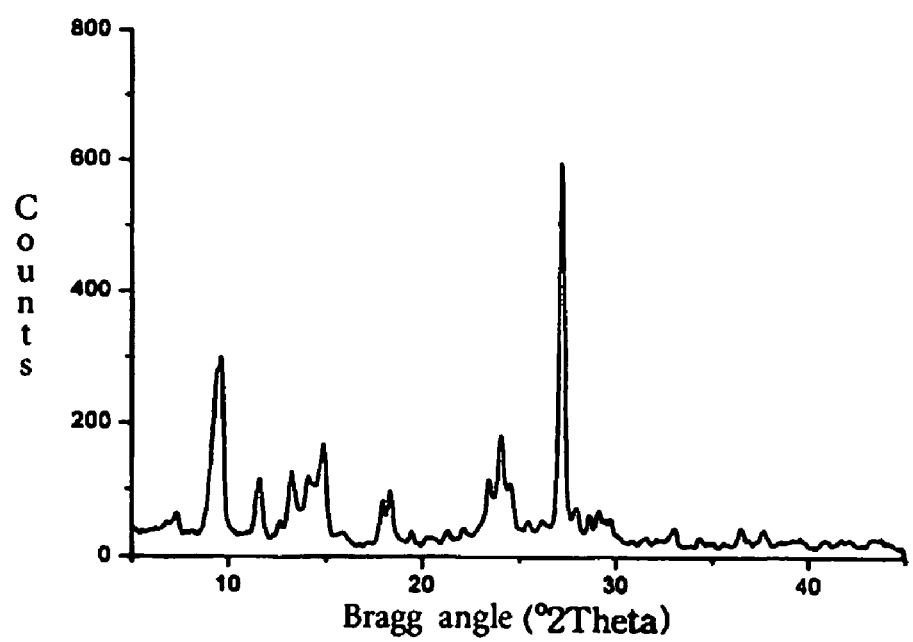
FIG. 10 is a graph showing the X-ray diffraction pattern of oxytitanium phthalocyanine prepared in Example 5 of the present invention.

5 g of the oxytitanium phthalocyanine prepared in Example 3 was dispersed in 20 g of tetrahydrofuran, left to stand for 5 days, filtered, and dried. The X-ray diffraction pattern of the dried oxytitanium phthalocyanine is shown in FIG. 10. This pattern shows that the gamma-form crystal of the oxytitanium phthalocyanine was maintained.

Comparative Example 4

Figure 11:
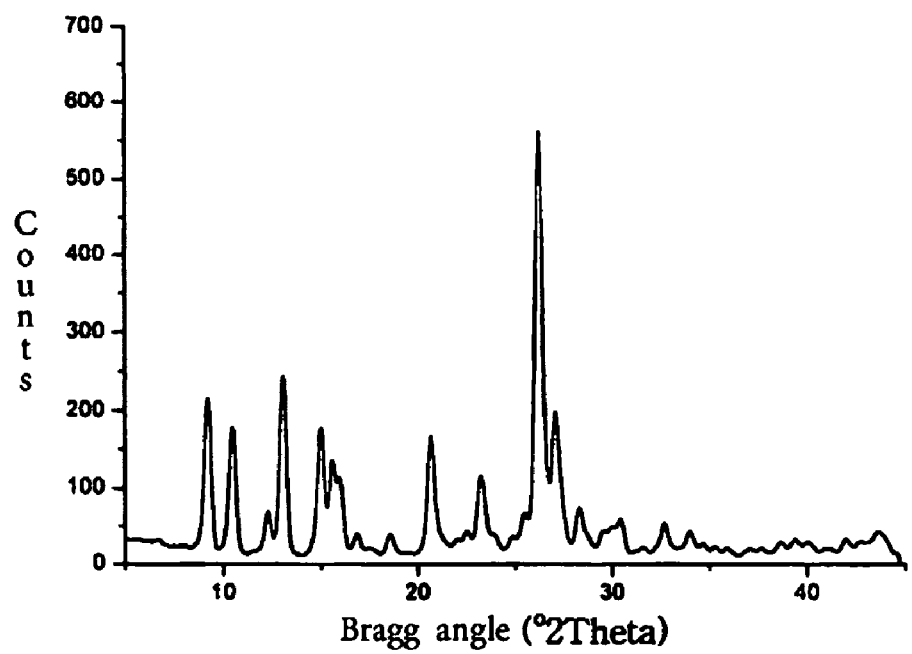
FIG. 11 is a graph showing the X-ray diffraction pattern of oxytitanium phthalocyanine prepared in Comparative Example 4 of the present invention.

5 g of the oxytitanium phthalocyanine prepared in Comparative Example 2 was dispersed in 20 g of tetrahydrofuran, left to stand for 5 days, filtered, and dried. The X-ray diffraction pattern of the dried oxytitanium phthalocyanine is shown in FIG. 11. This pattern shows that the gamma-form crystal was completely transformed into beta-form.

Example 6

Figure 12:
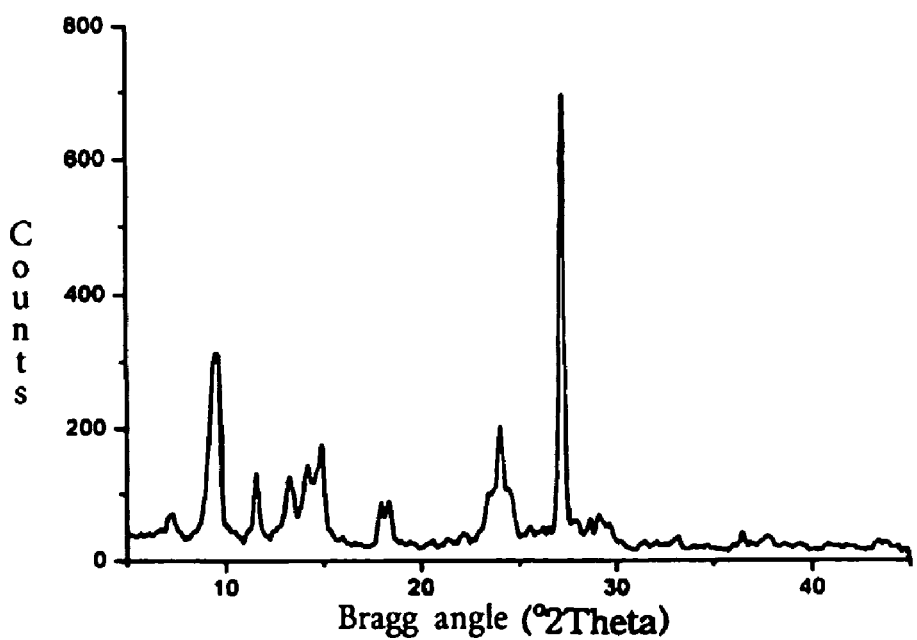
FIG. 12 is a graph showing the X-ray diffraction pattern of oxytitanium phthalocyanine prepared in Example 6 of the present invention.

9.8 g of an oxytitanium phthalocyanine charge generating material was prepared in the same manner as in Example 2, except that the oxytitanium phthalocyanine crude prepared in Synthesis 1 of Example 1 was used instead of that prepared in Synthesis 2 of Example 1. The X-ray diffraction pattern of the oxytitanium phthalocyanine charge generating material is shown in FIG. 12.

Example 7

Figure 13:
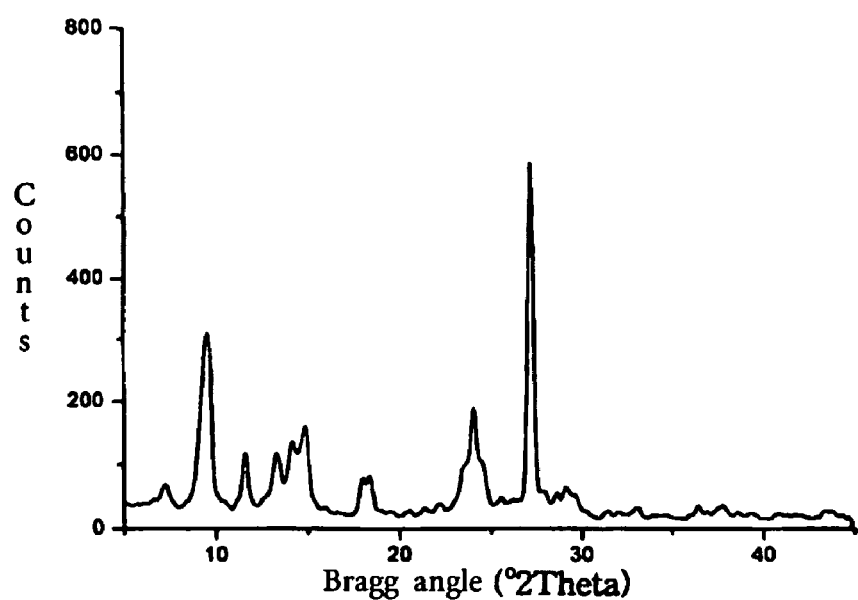
FIG. 13 is a graph showing the X-ray diffraction pattern of oxytitanium phthalocyanine prepared in Example 7 of the present invention.

5 g of the oxytitanium phthalocyanine prepared in Example 6 was dispersed in 20 g of tetrahydrofuran, left to stand for 5 days, filtered, and dried. The X-ray diffraction pattern of the dried oxytitanium phthalocyanine is shown in FIG. 13. This pattern shows that the gamma-form crystal was maintained.

Analytical Results of X-Ray Diffraction Patterns

Figure 2:
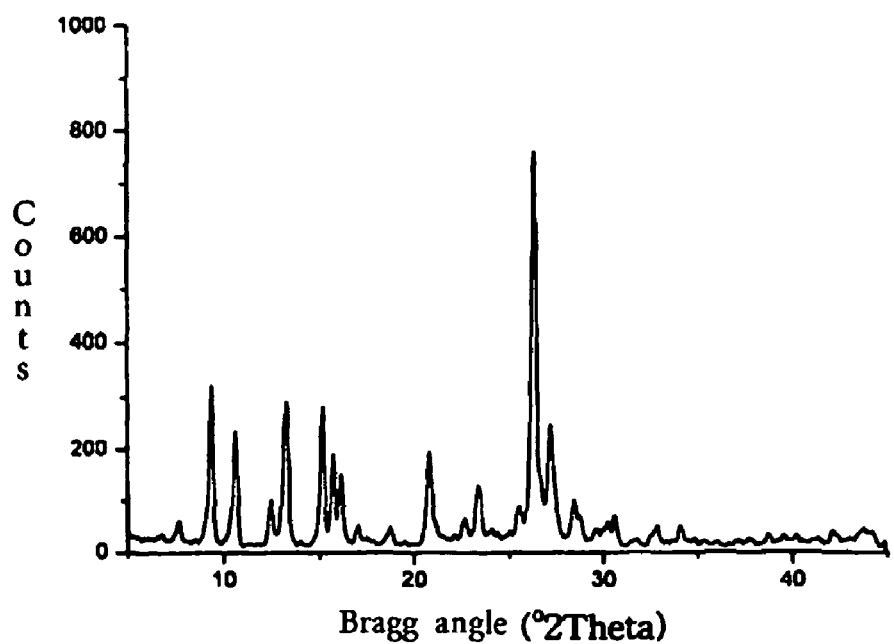
FIG. 2 is a graph showing the X-ray diffraction pattern of an oxytitanium phthalocyanine crude prepared in Example 1 (Synthesis 2) of the present invention.

As is evident from the X-ray diffraction pattern of the oxytitanium phthalocyanine crude prepared in Synthesis 1 of Example 1 using the apparatus of the present invention, one X-ray pattern peak was observed at a Bragg angle (2Theta) of 27.2±0.2° (see FIG. 1). This observation indicates that the crude has a novel crystal form. In contrast, as is clear from the X-ray diffraction pattern of the oxytitanium phthalocyanine crude prepared in Synthesis 2 of Example 1 using a conventional synthesis apparatus, typical peaks corresponding to beta-form were observed (see FIG. 2). These results reveal that the oxytitanium phthalocyanine crude prepared using the apparatus of the present invention has a different crystal form from that prepared using a conventional synthesis apparatus. Since the oxytitanium phthalocyanine crude prepared using the apparatus of the present invention shows one X-ray pattern peak at a Bragg angle of 27.2±0.2°, which is a characteristic peak of gamma-form crystal, and no diffraction peak inherent to beta-form crystal after the treatment, it has superior crystal stability. As can be seen from the X-ray diffraction patterns of the oxytitanium phthalocyanine charge generating materials prepared using the apparatus of the present invention, no diffraction peak was observed at a Bragg angle of 26.1±0.2° (FIGS. 4 to 6 and 12). Observation of the X-ray diffraction patterns indicates that all crystals were completely transformed into gamma-form crystals. In contrast, as is apparent from the X-ray diffraction patterns of the oxytitanium phthalocyanine charge generating materials prepared using a conventional apparatus, a distinct diffraction peak was observed at a Bragg angle of 26.1±0.2° (FIGS. 7 to 9, the circle shows an inherent characteristic peak of beta-form). This result indicates that the crystals have both gamma- and beta-forms. The higher the temperature, the more intense the beta-form peak. It is thus apparent that the oxytitanium phthalocyanine charge generating materials prepared using a conventional heat source are highly sensitive to temperature. Further, the characteristic peak of beta-form was observed even at a temperature as low as 50° C. In contrast, the oxytitanium phthalocyanine charge generating materials prepared using microwaves are gamma-form showing no characteristic peak of beta-form, and are less sensitive to temperature. In addition, the oxytitanium phthalocyanine charge generating materials prepared using microwaves had a larger peak intensity than the oxytitanium phthalocyanine charge generating materials prepared using a conventional heat source. Furthermore, since the oxytitanium phthalocyanine charge generating materials prepared using microwaves are gamma-form showing no characteristic peak of beta-form, they exhibit superior crystal stability against organic solvents. However, since the oxytitanium phthalocyanine charge generating materials prepared using a conventional heat source still have beta-form crystals, they have poor crystal stability against organic solvents and temperature and thus their gamma-form crystals are easily transformed into the more stable beta-form crystals.

Measurement of Electrophotographic Characteristics of Photoconductor Drums

Test Example 1

2.0 g of the oxytitanium phthalocyanine prepared in Example 2, 1.0 g of polyvinylbutyral, 40 g of tetrahydrofuran, and 110 g of glass beads (diameter: 1 mm) were dispersed in a paint shaker for 5 hours, and then 150 g of tetrahydrofuran was added thereto. The mixture was further dispersed for 10 minutes to prepare a coating solution for a charge generating layer. The coating solution was coated on the surface of an oxide film-coated aluminum drum to a thickness of 0.2 μm, and dried in a drier at 120° C. for 5 minutes.

Separately, 25 g of N,N'-bis(3-methylphenyl)-N,N'-diphenylbenzidine (Formula 2) and 25 g of poly(4,4-cyclohexylidene diphenylene carbonate) (Formula 3) were dissolved in 200 g of monochlorobenzene to prepare a coating solution for a charge transport layer.

Formula 2

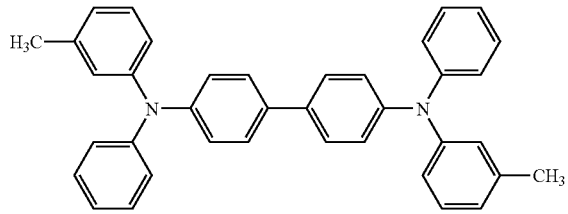

Formula 3

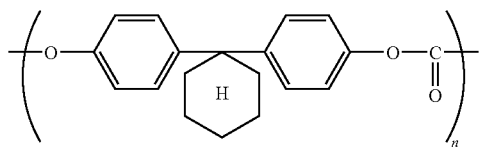

The coating solution for a charge-transport layer was coated on the charge generating layer-coated aluminum drum, and dried in a drier at 120° C. for 30 minutes to form a 20 μm thick charge transport layer, thereby producing a photoconductor drum.

The electrophotographic characteristics of the photoconductor drum were determined using an analyzer PDP-2000 (Quality Engineering Associates Inc., USA) in accordance with the following procedures.

1) Initial Surface Potential (VDDP)

When the photoconductor drum was charged by corona discharge at −60 kV, a potential generated on the surface of the photoconductor drum was measured.

2) Dark Decay (DD5)

3 seconds after the surface of the photoconductor drum was charged with a voltage of −700V, change in the potential of the drum surface was measured. The dark decay (DD5) was expressed in percent relative to the initial surface potential DD5 (%)=(surface potential 3 seconds after charging/ initial surface potential)×100

3) Sensitivity (E50%)

After the surface of the photoconductor drum was charged with a voltage of −700V and was then exposed to monochromatic light of a wavelength of 750 nm, the intensity of the monochromatic light required to reduce the surface potential of the drum to half of the initial surface potential of the drum was determined.

4) Final Potential (VF)

After the surface of the drum was charged with a voltage of −700V and was exposed to monochromatic light of a wavelength of 780 nm and an intensity of 13 J/cm$^2$, the surface potential was measured.

The obtained results are summarized in Table 1.

Test Examples 2 and 6

The procedures of Test Example 1 were repeated, except that the oxytitanium phthalocyanine charge generating materials prepared in Examples 3 to 7 were used. The results are summarized in Table 1.

Test Examples 7 to 10

The procedures of Test Example 1 were repeated, except that the oxytitanium phthalocyanine charge generating materials prepared in Comparative Examples 1 to 4 were used. The results are summarized in Table 1.

TABLE 1

Measurement results of electrophotographic characteristics

| Test Example No. | Charge generating materials | VDDP (V) | DD5 (%) | E50% (J/cm$^2$) | VF (V) |
|---|---|---|---|---|---|
| 1 | Example 2 | −713 | 95.4 | 0.100 | −48 |
| 2 | Example 3 | −718 | 95.6 | 0.102 | −49 |
| 3 | Example 4 | −713 | 95.7 | 0.100 | −44 |
| 4 | Example 5 | −691 | 92.3 | 0.102 | −50 |
| 5 | Example 6 | −750 | 96.8 | 0.086 | −32 |
| 6 | Example 7 | −721 | 95.1 | 0.095 | −45 |
| 7 | Comparative Example 1 | −689 | 91.5 | 0.130 | −56 |
| 8 | Comparative Example 2 | −691 | 91.5 | 0.125 | −51 |
| 9 | Comparative Example 3 | −687 | 91.4 | 0.129 | −68 |
| 10 | Comparative Example 4 | −531 | 70.5 | 0.398 | −53 |

INDUSTRIAL APPLICABILITY

As apparent from the foregoing, the present invention provides a method for preparing oxytitanium phthalocyanine as a charge generating material by synthesizing an oxytitanium phthalocyanine crude having a novel crystal form, and applying both microwaves and ultrasonic waves to the oxytitanium phthalocyanine crude. The method of the present invention is characterized in that the oxytitanium phthalocyanine crude shows one X-ray diffraction peak at a Bragg angle of 27.2±0.2°, and the oxytitanium phthalocyanine is completely gamma-form. In addition, since the oxytitanium phthalocyanine charge generating material has improved crystal stability against organic solvents and temperature, the method of the present invention can solve the conventional disadvantage of shortened shelf life caused after preparation of a coating solution for a charge generating layer. Furthermore, according to the method of the present invention, since small and uniform particles can be obtained, the time required for the preparation of a coating solution for a charge generating layer can be reduced, thus greatly improving the productivity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for preparing oxytitanium phthalocyanine as a charge generating material, comprising:
   homogeneously mixing an oxytitanium phthalocyanine crude with an organic solvent while microwave energy having a frequency of 0.1~100 GHz and a power of 10~3,000 W and ultrasonic wave energy having a frequency of 1~1,000 kHz and a power of 10~5,000 W are applied thereto; and
   reacting the mixture at 30~100° C. for 10 minutes~5 hours.

2. The method according to claim 1, wherein the oxytitanium phthalocyanine crude is dissolved in an acid and recrystallized, or dry- or wet-ground, before said mixing with said organic solvent.

3. The method according to claim 2, wherein the oxytitanium phthalocyanine crude is dissolved in an acid and recrystallized, and wherein the acid is sulfuric acid, phosphoric acid, or a halogenated carboxylic acid.

4. The method according to claim 2, wherein the oxytitanium phthalocyanine crude is dissolved in an acid and recrystallized, and wherein the solvent for the recrystallization is water, an aliphatic or aromatic alcohol, a ketone, an ether, an ester, or a mixed solution thereof.

5. The method according to claim 1, wherein the organic solvent is a halogenated benzene, a halogenated naphthalene, or an aqueous solution thereof.

6. The method according to claim 5, wherein the organic solvent is benzene or naphthalene substituted with 1 to 4 halogen atoms selected from chlorine, fluorine, bromine, and iodine.

7. The method according to claim 1, wherein the reaction is carried out at a temperature of 50~70° C.

8. The method according to claim 1, wherein the reaction time is 0.5 to 5 hours.

9. The method according to claim 1, wherein the oxytitanium phthalocyanine crude shows one X-ray diffraction peak at a Bragg angle of 27.2±0.2°.

10. An apparatus for preparing oxytitanium phthalocyanine as a charge generating material, comprising: a magnetron capable of generating a frequency of 0.1~100 GHz and a power of 100~3,000 W; a mode stirrer for making the wavelength of microwaves uniform in a microwave container; a PID type temperature controller for accurately measuring and controlling the temperature of reactants; a K-type thermocouple shielded from microwaves; a condenser; an agitator, the thermocouple, the condenser and the agitator being inserted into three openings formed at a top of the microwave container; an ultrasonic tip inserted into an opening formed at a bottom of the microwave container; a Pyrex container into which the reactants are introduced; and a solvent tank,
   wherein an oxytitanium phthalocyanine crude is homogeneously mixed with an organic solvent within the Pyrex container while microwave energy having a frequency of 0.1~100 GHz and a power of 10~3,000 W and ultrasonic wave energy having a frequency of 1~,000 kHz and a power of 10~5,000 W are applied thereto, and the reactants are reacted with each other at a temperature of 30~100° C. for 10 minutes~5 hours while the temperature of the reactants is accurately controlled by the K-type thermocouple and the PID type temperature controller.

11. The apparatus according to claim 10, wherein the oxytitanium phthalocyanine crude is dissolved in an acid at room temperature or more and recrystallized, or dry- or wet-ground before use.

12. The apparatus according to claim 11, wherein the acid is sulfuric acid, phosphoric acid, or a halogenated carboxylic acid.

13. The apparatus according to claim 11, wherein the solvent for the recrystallization is water, an aliphatic or aromatic alcohol, a ketone, an ether, an ester, or a mixed solution thereof.

14. The apparatus according to claim 10, wherein the organic solvent is a halogenated benzene, a halogenated naphthalene, or an aqueous solution thereof.

15. The apparatus according to claim 14, wherein the halogenated benzene or halogenated naphthalene is benzene or naphthalene substituted with 1 to 4 halogen atoms selected from chlorine, fluorine, bromine, and iodine.

16. The apparatus according to claim 10, wherein the reaction is carried out at a temperature of 50~70° C.

17. The apparatus according to claim 10, wherein the reaction time is in the range of from 0.5 to 5 hours.

18. The apparatus according to claim 10, wherein the oxytitanium phthalocyanine crude shows one X-ray diffraction peak at a Bragg angle of 27.2±0.2°.

19. An oxytitanium phthalocyanine charge generating material prepared by the method according to claim 1 wherein the charge generating material shows X-ray diffraction peaks at Bragg angles of 7.2±0.2°, 9.6°±0.2°, 11.7°±0.2°, 12.7°±0.2°, 13.4°±0.2°, 14.1°±0.2°, 14.8°±0.2°, 18.0°±0.2°, 18.4°±0.2°, 22.3°±0.2°, 23.4°±0.2°, 24.1°±0.2°, 24.5°±0.2°, and 27.2°±0.2°.

20. A photoconductor produced using the oxytitanium phthalocyanine charge generating material according to claim 19.

* * * * *

UNITED STATES PATENT AND TRADEMARK OFFICE
CERTIFICATE OF CORRECTION

PATENT NO. : 7,812,154 B2  
APPLICATION NO. : 10/574797  
DATED : October 12, 2010  
INVENTOR(S) : Jong Ho Kwon et al.

It is certified that error appears in the above-identified patent and that said Letters Patent is hereby corrected as shown below:

ON THE TITLE PAGE:

Item (57), Abstract (line 13-14), "2; a PID type temperature controller 9 for accurately measurement and controlling the temperature of reactants; a" should read --2; a PID type temperature controller 9 for accurately measuring and controlling the temperature of reactants; a--

Signed and Sealed this
Third Day of January, 2012

David J. Kappos
*Director of the United States Patent and Trademark Office*